US00H002246H

(19) United States
(12) Statutory Invention Registration
Miller et al.

(10) Reg. No.: US H2246 H
(43) Published: Aug. 3, 2010

(54) METHOD FOR ANALYZING CONTINUOUS GLUCOSE MONITORING DATA

(75) Inventors: Michael Franklin Miller, Langhorne, PA (US); Poul Strange, Princeton Junction, NJ (US)

(73) Assignee: Aventis Pharmaceuticals Inc., Bridgewater, NJ (US)

(21) Appl. No.: 11/713,965

(22) Filed: Feb. 28, 2007

Related U.S. Application Data

(60) Provisional application No. 60/863,937, filed on Nov. 1, 2006, and provisional application No. 60/863,673, filed on Oct. 31, 2006.

(51) Int. Cl.
*A61B 5/00* (2006.01)

(52) U.S. Cl. ..... 600/365; 600/366; 600/347; 600/316; 600/319

(58) Field of Classification Search ..... 600/365, 600/366, 347, 316, 319
See application file for complete search history.

(56) References Cited

U.S. PATENT DOCUMENTS 5,533,509 A * 7/1996 Koashi et al. ..... 600/316
6,370,407 B1 * 4/2002 Kroeger et al. ..... 600/319
6,574,490 B2 * 6/2003 Abbink et al. ..... 600/316
6,650,915 B2 * 11/2003 Routt et al. ..... 600/319

* cited by examiner

*Primary Examiner*—Michelle Clement
(74) *Attorney, Agent, or Firm*—Synnestvedt & Lechner LLP

(57) ABSTRACT

A method for predicting the effectiveness of medication-based therapy in lowering average blood glucose levels in a diabetic patient is provided. This method may further comprise selectively recommending a medication-based therapy on the basis of the arithmetic average of the relative minima. A method for determining susceptibility to symptomatic hypoglycemia in a patient is provided. This method may further comprise selectively recommending a medication-based therapy on the basis of the arithmetic average of the relative minima. Provided also is a device for continuously monitoring blood glucose levels in a patient. The methods and device involve applying a Fourier approximation to blood glucose level data.

9 Claims, 6 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

Figure 1A: 24-Hour BG Levels in 1 Patient with T2DM (Fourier Approximation: 5 Cycles)
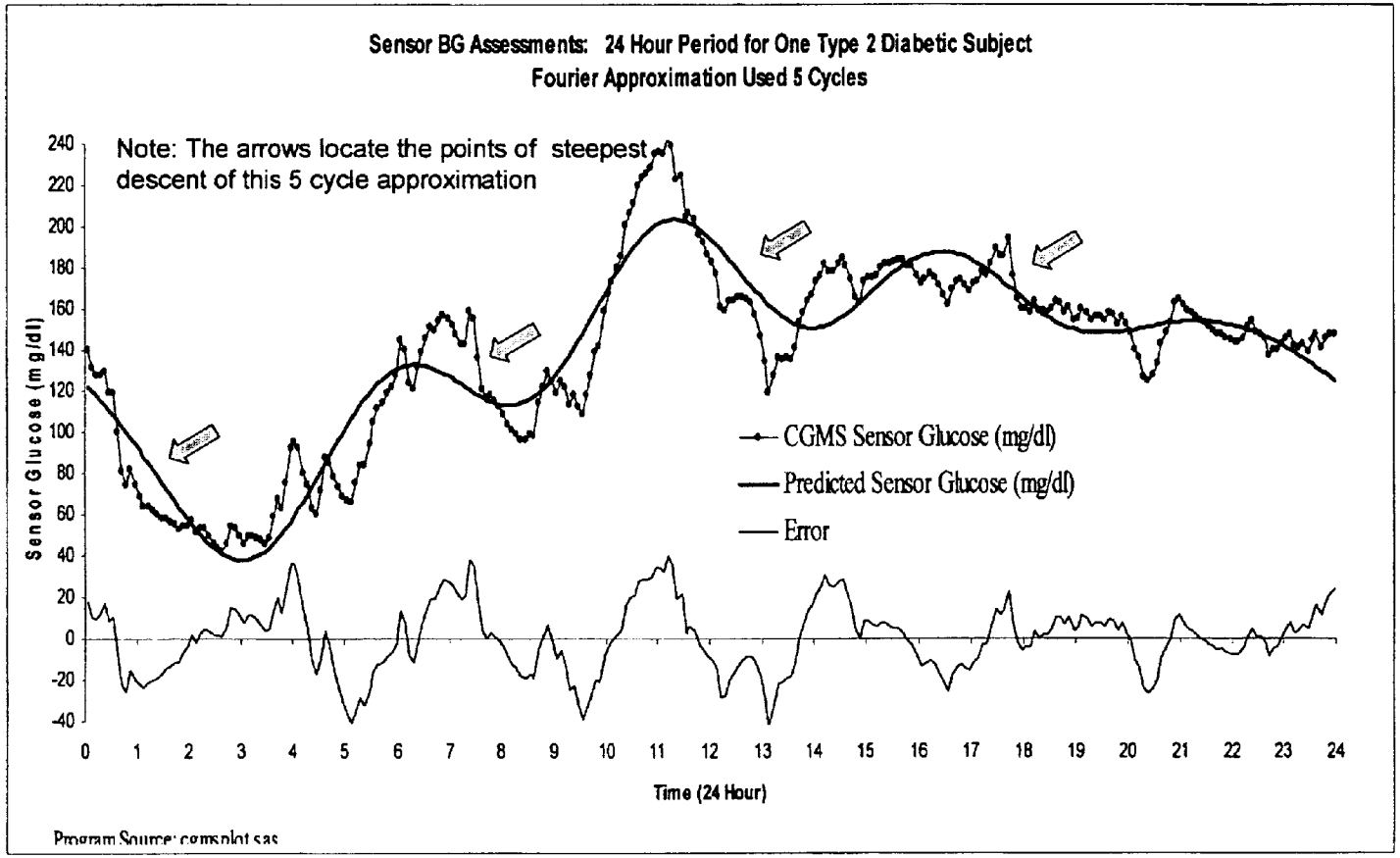

Figure 1B: 24-Hour BG Levels in the Same Patient (Fourier Approximation: 20 Cycles)
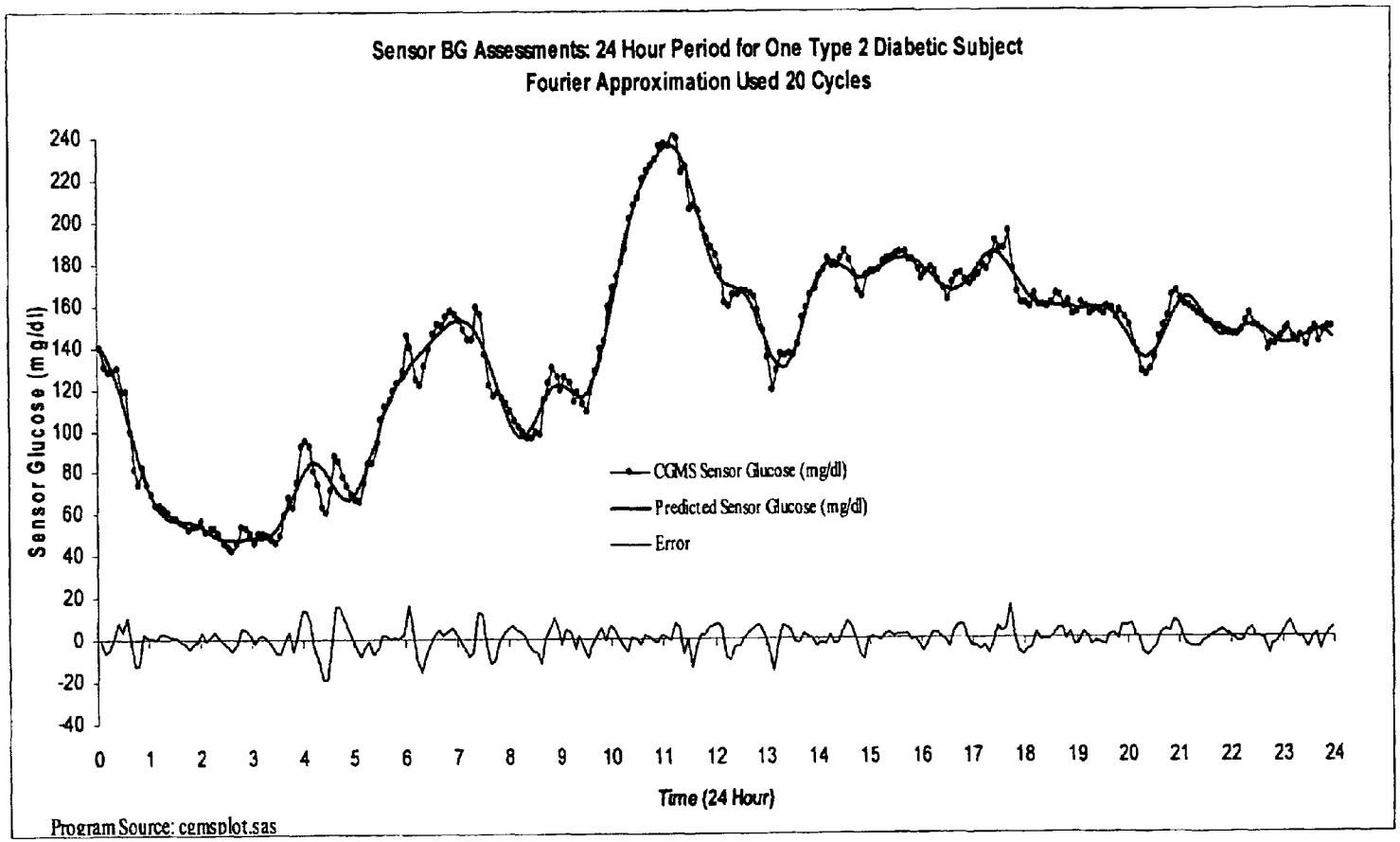

Figure 2: Dimension Reduction of Asynchronous CGMS Profiles Important Information Is Retained
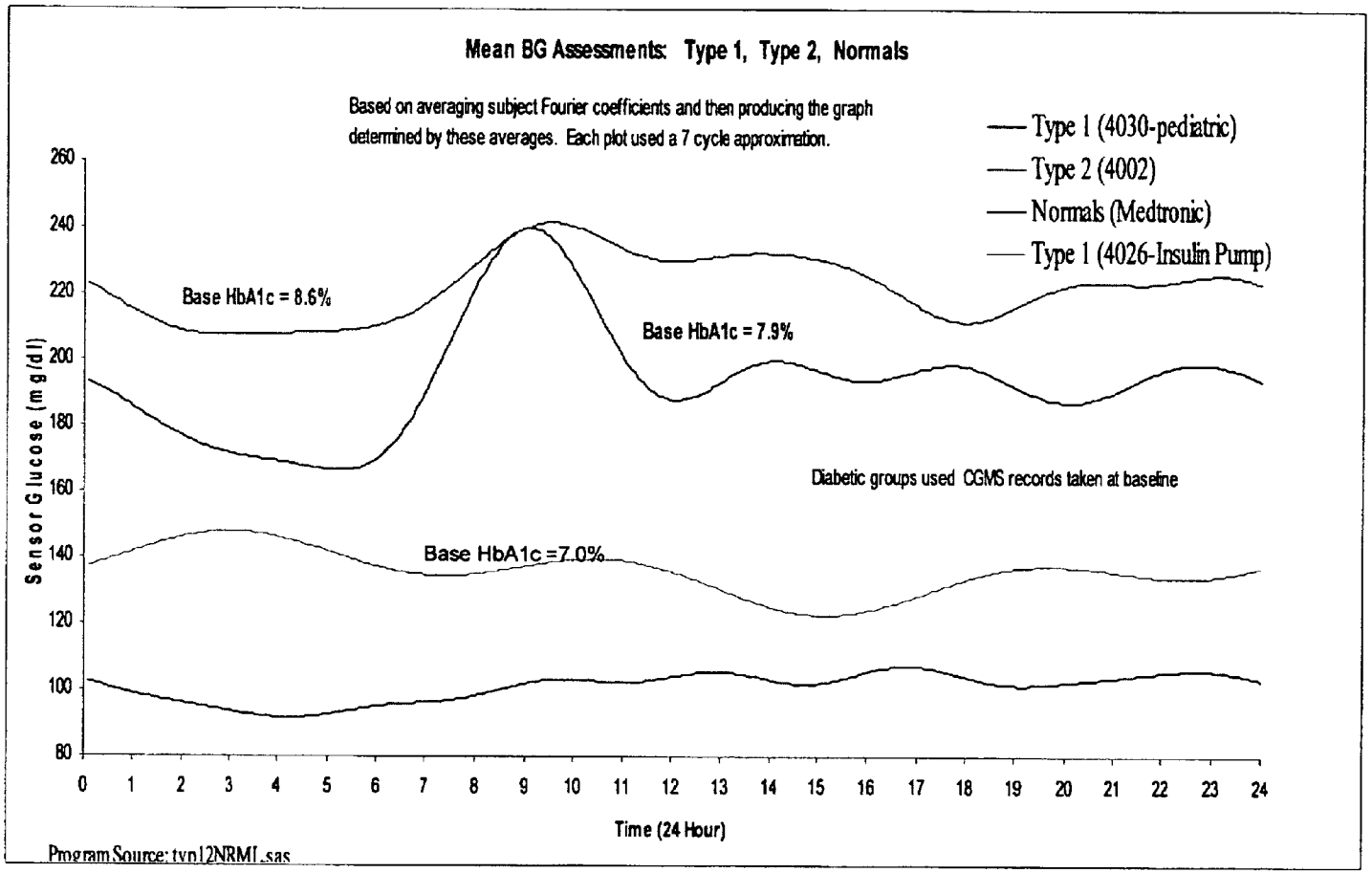

Figure 3: Plot of Component Harmonics at Baseline in Pediatric Patients with T1DM (n=90)
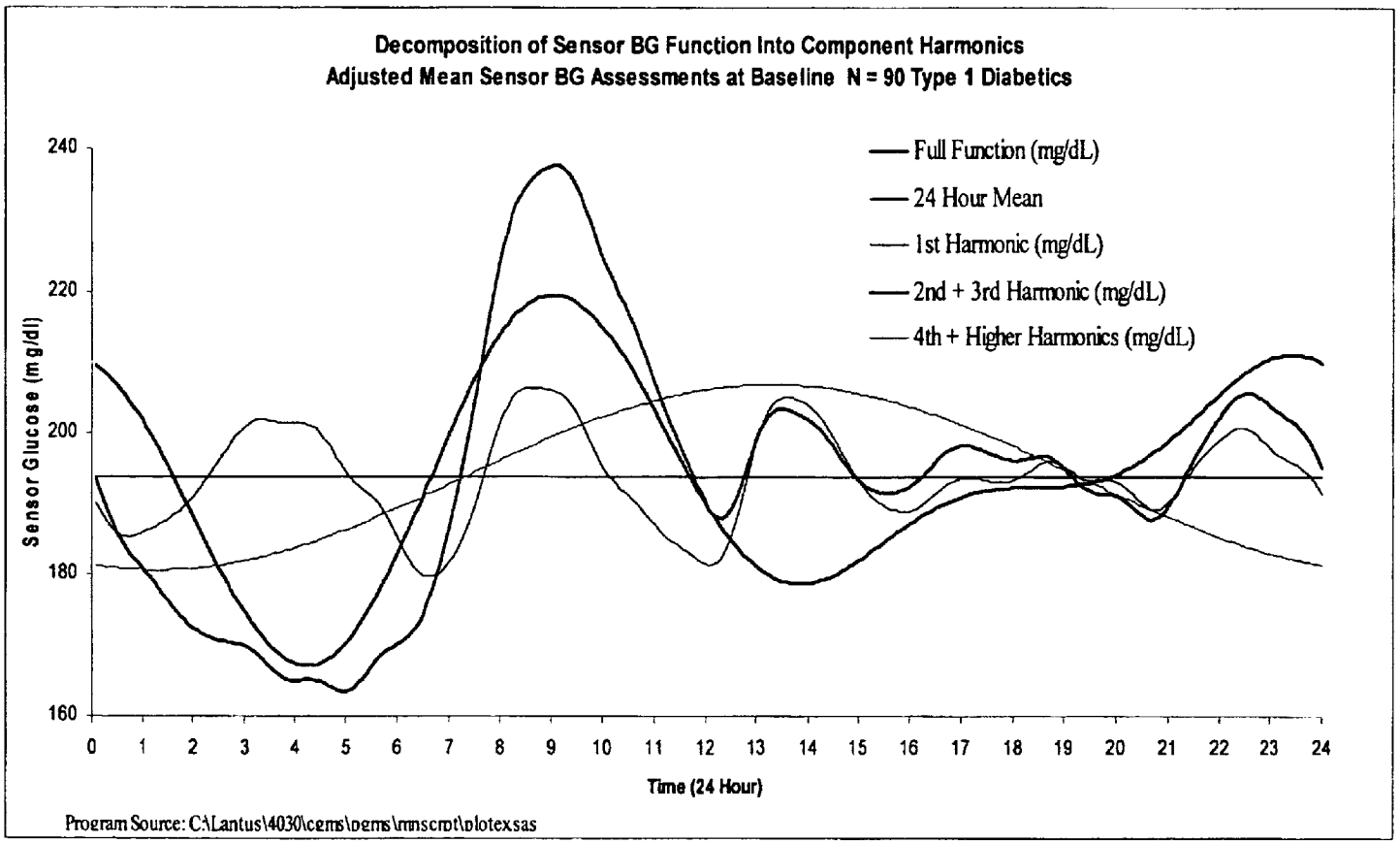
Note: 2nd + 3rd Harmonic = sum of the 2nd and 3rd Fourier estimated harmonic functions

Figure 4: Baseline Amplitude of 2nd + 3rd Harmonic Functions Associated With Week 24 HbA1c in Pediatric Patients With T1DM
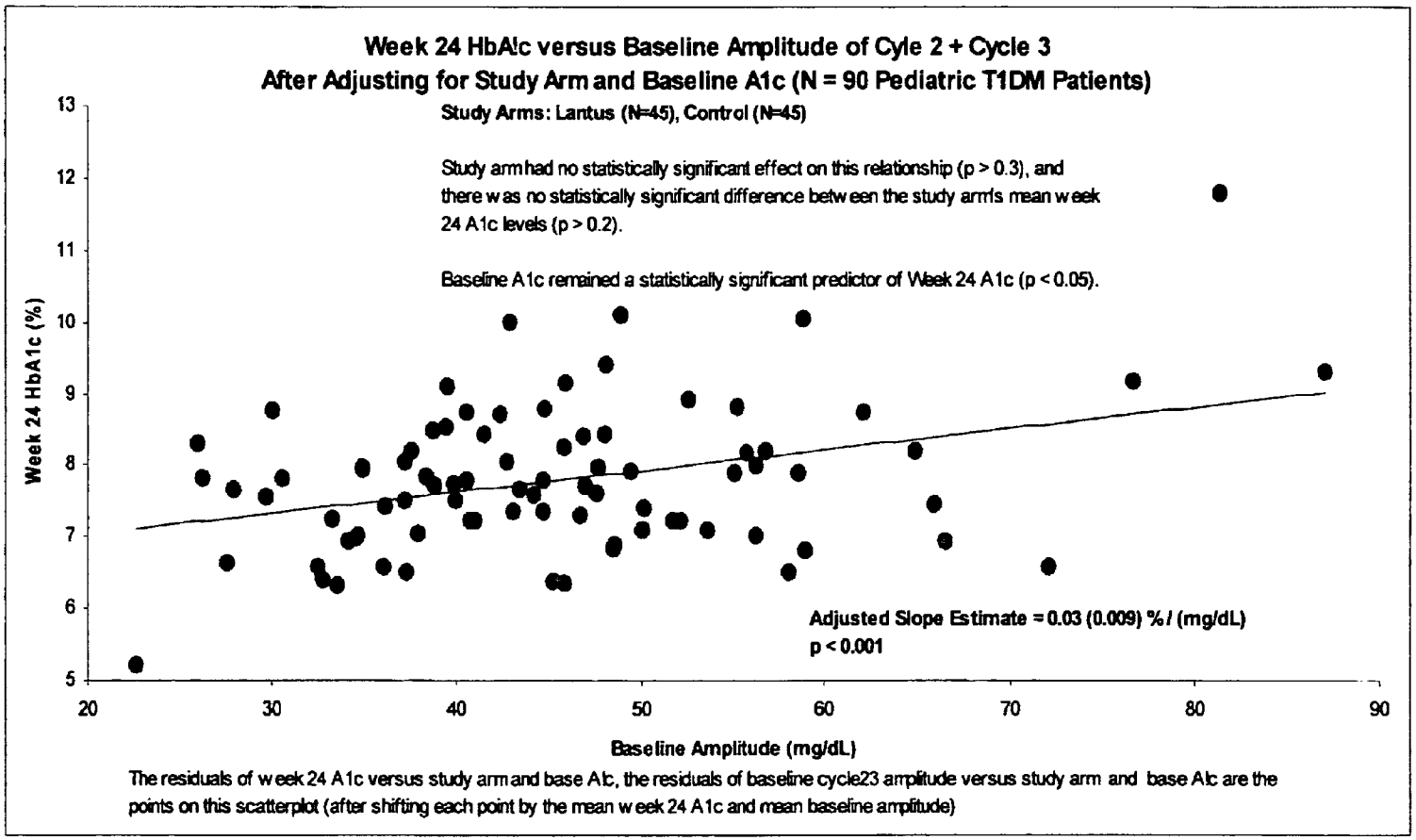

Figrure 5: Baseline Average Steepest Descent Associated With Hypoglycemia in Pediatric Patients With T1DM
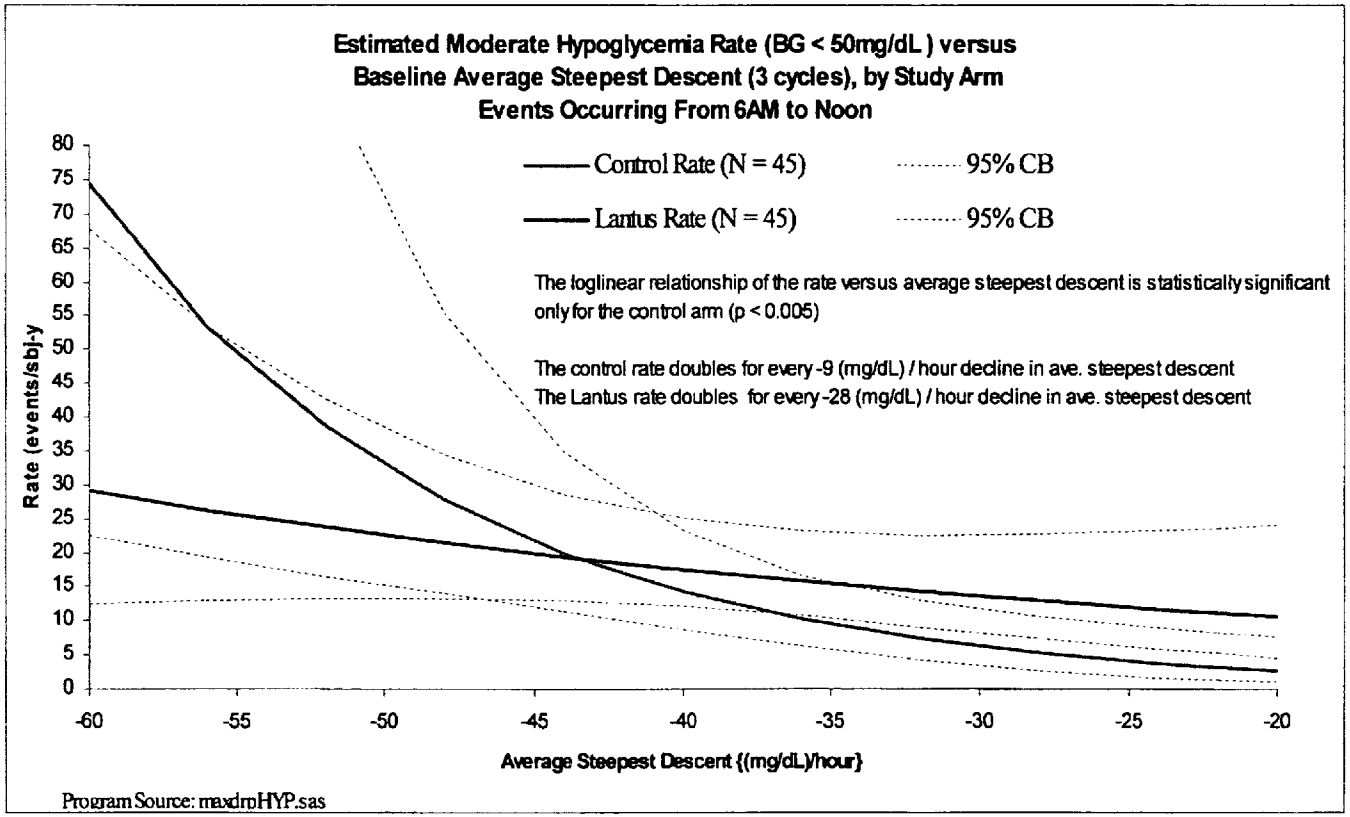

METHOD FOR ANALYZING CONTINUOUS GLUCOSE MONITORING DATA

CROSS REFERENCE TO RELATED APPLICATIONS

This application is related to U.S. application Ser. No. 60/863,673, filed Oct. 31, 2006, the entire disclosure of which is hereby incorporated herein by reference.

FIELD OF INVENTION

The present invention relates, generally, to methods for analyzing continuous glucose monitoring data. More specifically, the invention relates to methods for determining a patient's susceptibility to hypoglycemic events and methods for predicting the effectiveness of insulin therapy in lowering average blood glucose levels in a diabetic patient.

BACKGROUND OF INVENTION

Diabetics must monitor their own blood glucose levels, often several times a day, to determine how far above or below a normal level their glucose level is and to determine what oral medications or insulin(s) they may need. This is often done by placing a drop of blood from a skin prick onto a glucose strip and then inserting the strip into a glucose meter, which is a small machine that provides a digital readout of the blood glucose level.

Recently, continuous glucose monitoring systems (CGMS) have been developed that continuously record a patient's glucose levels throughout the day. Generally speaking, these devices work by inserting a small sensor into subcutaneous tissues. The sensor measures the level of glucose in the tissue and sends this information to a monitor worn by the patient which stores the results, In order to determine blood glucose levels, the monitor must be calibrated daily by entering at least three blood glucose readings obtained at different times, using a standard blood glucose meter. For example, Medtronic, Inc. of Minneapolis, Minn., sells an approved MinMed® device which can provide up to 288 glucose measurements every 24 hours for up to 72 hours.

One problem with the blood glucose level data obtained from continuous glucose monitoring systems is that there is a lot of variability in the data. The glucose level data shows a lot of sharp fluctuations, or signal noise, that is most likely not indicative of the average blood glucose levels, but rather is likely due to variability in the measurements.

Because of the lack of accurate diary data from patients and the lack of mealtime synchronization, another problem with CGMS data is the inability to aggregate the data easily to facilitate treatment group comparisons and to visualize the average treatment group curves.

As a result of the problems indicated above, a further problem is the lack of CGMS data indicators that would be useful for diagnosing and treating hypoglycemia and diabetes.

Therefore, there is a need to aggregate continuous blood glucose level data and to identify prognostic indicators for diagnosing and treating hypoglycemia and diabetes.

SUMMARY OF THE INVENTION

One aspect of the present invention relates to a method for predicting the effectiveness of medication-based therapy in lowering average blood glucose levels in a diabetic patient comprising the steps of: measuring the patient's blood glucose levels continuously for a period of time to obtain blood glucose level data; applying a Fourier approximation to develop a continuous oscillating blood glucose curve approximately representing the blood glucose level data; mathematically decomposing oscillation of the blood glucose curve into at least one respective component harmonic curve; calculating an amplitude of a composite curve that is a function of the at least one respective component harmonic curve; and correlating the amplitude of the composite curve with an expectation that medication-based therapy will lower the average blood glucose levels in a diabetic patient. This method may further comprise selectively recommending a medication-based therapy on the basis of the arithmetic average of the relative minima.

Another aspect of the invention is a method for determining susceptibility to symptomatic hypoglycemia in a patient comprising the steps of: measuring the patient's blood glucose levels continuously for a period of time to obtain blood glucose level data; applying a Fourier approximation to develop a continuous oscillating blood glucose curve approximately representing the blood glucose level data; identifying areas of the curve having steepest descent, the areas of steepest descent corresponding to relative minima of a first derivative of the curve; calculating an arithmetic average of the relative minima; and correlating a high arithmetic average of the relative minima with an increased susceptibility to symptomatic hypoglycemia. This method may further comprise selectively recommending a medication-based therapy on the basis of the arithmetic average of the relative minima.

Another aspect of the invention is a device for continuously monitoring blood glucose levels in a patient comprising: a sensor for measuring blood glucose levels in said patient; a monitor for recording blood glucose levels at regular intervals; and software executable by said monitor for applying a Fourier approximation to said blood glucose levels.

BRIEF DESCRIPTION OF DRAWINGS

FIG. 1A shows an exemplary graph of blood glucose level data from an exemplary type 2 diabetes mellitus patient using a CGMS sensor. The graph also shows a Fourier approximation (5 cycles) of the blood glucose level data and the error between the blood glucose level data and the Fourier approximation.

FIG. 1B shows an exemplary graph of blood glucose levels from an exemplary type 2 diabetes mellitus patient using a CGMS sensor. The graph also shows a Fourier approximation (20 cycles) of the blood glucose level data and the error between the blood glucose level data and the Fourier approximation.

FIG. 2 shows an exemplary graph of the mean Fourier approximations (7 cycles) of the blood glucose levels of exemplary type 1 diabetes mellitus patients, exemplary type 2 diabetes mellitus patients, exemplary normal subjects, and exemplary type 1 diabetes mellitus patients using an insulin pump.

FIG. 3 shows an exemplary graph of the mean blood glucose levels from exemplary type 1 diabetes mellitus patients using a CGMS sensor along with the first, the sum of the second and third, and the sum of the fourth and higher harmonic functions of a Fourier approximation of the mean blood glucose level data.

FIG. 4 shows an exemplary graph of week twenty-four HbA1c levels versus the mean baseline amplitude of the sum of the second and third harmonic functions of a Fourier approximation.

FIG. 5 shows an exemplary graph of rate of hypoglycemic events versus baseline average steepest descent from a Fourier approximation (3 cycles) of mean blood glucose level data from exemplary pediatric patients with type 1 diabetes mellitus treated with Lantus® (insulin glargine) manufactured and distributed by sanofi-aventis and a control medication.

DETAILED DESCRIPTION

The present invention relates, generally, to methods for analyzing continuous glucose monitoring data. In order to minimize the impact of sharp fluctuations in CGMS data and to have the ability to aggregate CGMS data from various patient populations, applicants have applied the Fourier approximation method to patient CGMS data.

The Fourier approximation method provides a statistical model for assessing a patient's whole blood glucose profile over a period of time. The Fourier approximation method results in the smoothing out of extraneous variability in the CGMS data via dimension reduction. By applying a Fourier approximation to CGMS data, one can separate the blood glucose profile into a mean level and variability components which can be further partitioned into component harmonics.

The Fourier approximation method can be applied to blood glucose levels in the following manner. For example, levels of blood glucose over a given period of time can be defined as the function CGMS(t). The Fourier approximation of the function CGMS(t) can be designated as FR(t|k) where CGMS(t)=FR(t|k). Where t is measured in hours and ranges from 0 to 24 and harmonic term i oscillates through exactly i cycles in 24 hours, the Fourier approximation is calculated as follows:

$$=\mu+\Sigma_i \mathrm{AMP}(i)\cos(2\pi i\ (t-\mathrm{PHS}\ (i))/24)$$

$$=\mu+\Sigma_i\{\mathrm{A}(i)\cos(2\pi i\ t/24)+\mathrm{B}(i)\sin(2\pi i\ t/24)\}$$

where $\mu$=CGMS 24-hour mean=AUC/24

A($i$), B($i$) regression coefficients for cycle i, i=1 to k

Amplitude of harmonic term i=sqrt($\mathrm{A}(i)^2+\mathrm{B}(i)^2$)

Phase shift for harmonic term i=arctan(B($i$)/A($i$))

Individual components of the Fourier approximation can be used to measure the clinical outcomes for the treatment of hypoglycemia or diabetes. For example, if the clinical outcome is reducing the blood glucose levels, one would measure the first term in the Fourier expansion, the twenty-four hour mean blood glucose level. Similarly, if the goal is to reduce the risk of hypoglycemic and hyperglycemic events, one would measure the harmonic amplitudes. Furthermore, the CGMS twenty-four hour standard deviation is proportional to the square root of the sum of the squares of the individual amplitudes of all component harmonic functions. Thus, a reduction of the standard deviation of CGMS levels can be measured by a reduction of the Fourier harmonic component amplitudes.

EXAMPLES

Example 1

A Fourier approximation is applied to the observed CGMS blood glucose data for one patient with type 2 diabetes mellitus. FIG. 1A shows a Fourier approximation of the CGMS data using five cycles calculated as described above. FIG. 1B shows a Fourier approximation of the same data using twenty cycles. As seen in the FIGS. 1A and 1B, the Fourier approximations tend to smooth out the high-frequency noise observed in the raw CGMS data. As one increases the number of cycles, the Fourier approximation does a better job of approximating the actual CGMS data as shown by the decrease in the fluctuation of the error graph in FIG. 1B as compared to FIG. 1A. As one increases the number of cycles, however, the smoothness of the Fourier approximation curve is decreased, resulting in a curve that is less likely to be useful in identifying prognostic indicators.

Example 2

This study employs CGMS 24-hour blood glucose profiles from the following patient populations:

pediatric patients with type 1 diabetes mellitus (T1DM), N=90;

adult patients with type 2 diabetes mellitus (T2DM), N=34;

normal subjects, N=15; and patients with T1DM using an insulin pump, N=37.

For each subject, a seven cycle Fourier approximation is applied to twenty-four hour CGMS data. An aggregate curve is created for each patient population by averaging the subject Fourier coefficients and producing a graph determined by these averages. FIG. 2 shows the resulting graphs for each patient population. An interesting observation is that insulin-pump therapy not only reduces the average blood glucose levels but also reduces the amplitude of the resulting aggregate Fourier approximation. This indicates that type 1 patients using the insulin pump are less likely to experience hypoglycemic and hyperglycemic events.

Example 3

This study employs CGMS 24-hour blood glucose profiles from the pediatric patients with type 1 diabetes mellitus (T1DM), N=90; half of the patients are on a typical insulin therapy regimen while half of the patients are using Lantus®. For each subject, a Fourier approximation is applied to twenty-four hour CGMS data. An aggregate curve is created for the patient population by averaging the subject Fourier coefficients and producing a graph determined by these averages. The Fourier approximation is decomposed into its component harmonics. FIG. 3 shows the resulting graph of the mean blood glucose levels from the patient population along with the first, the sum of the second and third, and the sum of the fourth and higher harmonic functions of the aggregate Fourier approximation.

FIG. 4 shows a graph of week twenty-four HbA1c levels versus the mean baseline amplitude of the sum of the second and third harmonic functions of a Fourier approximation. HbA1c is a specific subtype of hemoglobin A. Hemoglobin A comprises about 90% of the total hemoglobin in red blood cells. When glucose binds to hemoglobin A, it forms the A1c subtype. This reaction and the reverse reaction, or decomposition, proceeds relatively slowly, so any buildup persists for roughly four weeks. As a result, the HbAlc level correlates very well with the average blood glucose level of approximately the past 4 weeks. In normal subjects, the HbAlc reach a steady state of about 4 to 5% of the hemoglobin being the A1c subtype. Accordingly, the HbA1c level is a good proxy of average blood glucose levels.

FIG. 4 shows a correlation between the amplitude of the sum of the second and third harmonic functions of a Fourier approximation in type 1 diabetic patients with week 24 HbA1c levels. For fixed-baseline HbA1C, higher amplitude of the sum of the 2nd and 3rd harmonic functions (a composite curve) at baseline predicted higher week twenty-four HbA1C values in pediatric patients with T1DM. Accordingly, the amplitude of the sum of the second and third harmonic functions of a Fourier approximation (the composite second and third harmonic curve) may be useful in predicting the effectiveness of medication-based therapy in lowering average blood glucose levels in a type 1 diabetic patient.

This correlation may be used, for example, as a basis for selectively recommending a medication-based therapy on the basis of the amplitude of the composite curve, e.g. to recommend the medication-based therapy if the amplitude exceeds a predetermined, empirically set, amplitude threshold. For example, the threshold and decision-based logic may be implemented by software executable by a special-purpose CGMS device configured in accordance with the present invention or a conventional personal computer (collectively, a "PC"), and the recommendation may be textual, graphical or other indicia displayed on a display screen of the PC, etc. to a prescribing physician, etc.

Example 4

This study employs CGMS 24-hour blood glucose profiles from the pediatric patients with type 1 diabetes mellitus (T1DM), N=90; half of the patients are on a typical insulin therapy regimen while half of the patients are using Lantus®. For each patient, Fourier approximation using 3 cycles is applied to a 24-hour CGMS profile. The areas of the curve having the steepest descent are identified, the areas of steepest descent corresponding to the relative minima of a first derivative of the curve (e.g., as determined by zeros of the second derivative of the curve). The average steepest descent is calculated by mathematically calculating the arithmetic average of the relative minima.

FIG. 5 shows the resulting graph of the rate of hypoglycemic events in both the control and Lantus® populations versus the baseline average steepest descent as described above. As FIG. 5 indicates, the average steepest descent at baseline has an association with symptomatic hypoglycemia (with BG<50 mg/dL). Thus, baseline steep descent of blood glucose levels may increase the risk of hypoglycemia at certain times in pediatric patients with T1DM. Accordingly, the average steepest descent of Fourier approximations of CGMS data may be useful for determining susceptibility to symptomatic hypoglycemia in a patient.

This determination for susceptibility may be used, for example, as a basis for selectively recommending a medication-based therapy on the basis of the arithmetic average of the relative minima, e.g. to recommend the medication-based therapy if the average exceeds a predetermined, empirically set, average threshold. For example, the threshold and decision- based logic may be implemented by software executable by a special-purpose CGMS device configured in accordance with the present invention, a conventional personal computer (collectively, a "PC"), and the recommendation may be textual, graphical or other indicia displayed on a display screen of the PC, etc. to a prescribing physician, etc.

A device for continuously monitoring blood glucose levels in a patient may include a conventional sensor for measuring blood glucose levels in the patient and a conventional monitor for recording blood glucose levels at regular intervals. In accordance with the present invention, a substantially conventional CGMS device may be specially configured in accordance with the present invention to include software executable by the monitor for applying a Fourier approximation to the blood glucose level data, determining composite harmonic curve amplitudes, determining average steepest descent, determining susceptibility to symptomatic hypoglycemia, storing threshold data, selectively recommending medication-based therapy as a function of a relationship to stored threshold data, etc., as discussed in greater detail above. By way of further example, the device may be capable of exporting gathered data to a personal computer or other external computing device configured with similar specially configured software for providing such functionality.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method implemented on a CGMS device for predicting the effectiveness of medication-based therapy in lowering average blood glucose levels in a diabetic patient comprising the steps of:

measuring by a sensor said patient's blood glucose levels continuously for a period of time to obtain blood glucose level data and providing said measured glucose levels to a CGMS device;

applying by the CGMS device a Fourier approximation to develop a continuous oscillating blood glucose curve approximately representing the blood glucose level data;

mathematically decomposing by the CGMS device oscillation of the blood glucose curve into at least one respective component harmonic curve;

calculating by the CGMS device an amplitude of a composite curve that is a function of the at least one respective component harmonic curve; and correlating by the CGMS device the amplitude of the composite curve with an expectation that medication-based therapy will lower the average blood glucose levels in a diabetic patient.

2. The method of claim 1, wherein the function of the at least one respective component harmonic curve is a sum of amplitudes of second and third component harmonic curves.

3. The method of claim 1 further comprising selectively recommending a medication-based therapy on the basis of the amplitude of the composite curve.

4. The method of claim 1, wherein said period of time is twenty-four hours.

5. The method of claim 1, wherein said patient has type 1 diabetes mellitus.

6. A method implemented on a CGMS device for determining susceptibility to symptomatic hypoglycemia in a patient comprising the steps of:

measuring by a sensor said patient's blood glucose levels continuously for a period of time to obtain blood glucose level data and providing said measured glucose levels to a CGMS device;

applying by the CGMS device a Fourier approximation to develop a continuous oscillating blood glucose curve approximately representing the blood glucose level data;

identifying by the CGMS device areas of the curve having the steepest descent, the areas of steepest descent corresponding to relative minima of a first derivative of the curve;

calculating by the CGMS device an arithmetic average of the relative minima; and correlating by the CGMS device a high arithmetic average of the relative minima with an increased susceptibility to symptomatic hypoglycemia.

7. The method of claim 6 further comprising selectively recommending a medication-based therapy on the basis of the arithmetic average of the relative minima.

8. The method of claim 6, wherein said period of time is 24 hours.

9. A device of continuously monitoring blood glucose levels in a patient comprising:

a sensor for measuring blood glucose levels in said patient;

a monitor for recording blood glucose levels at regular intervals; and software executable by said monitor for applying a Fourier approximation to said blood glucose levels.

* * * * *